(12) United States Patent
Kosecoff

(10) Patent No.: US 12,027,268 B2
(45) Date of Patent: Jul. 2, 2024

(54) DEVICE FOR MEASURING SKIN EXPOSURE TO POLLUTANTS OR PROXIMITY TO POLLUTANT SOURCES AND RECOMMENDING PERSONALIZED SKINCARE PRODUCTS

(71) Applicant: L'Oreal, Paris (FR)

(72) Inventor: David B. Kosecoff, San Francisco, CA (US)

(73) Assignee: L'Oreal, Paris (FR)

( * ) Notice: Subject to any disclaimer, the term of this patent is extended or adjusted under 35 U.S.C. 154(b) by 270 days.

(21) Appl. No.: 17/084,269

(22) Filed: Oct. 29, 2020

(65) Prior Publication Data

US 2022/0139551 A1   May 5, 2022

(51) Int. Cl.
*G16H 50/20* (2018.01)
*A61B 5/00* (2006.01)
*G06Q 30/0601* (2023.01)
*G16H 10/60* (2018.01)
*G16H 40/67* (2018.01)
*G16H 50/30* (2018.01)
(Continued)

(52) U.S. Cl.
CPC ......... *G16H 50/20* (2018.01); *G06Q 30/0631* (2013.01); *G16H 10/60* (2018.01); *G16H 50/30* (2018.01); *G16H 50/50* (2018.01); *A61B 5/445* (2013.01); *G16H 40/67* (2018.01); *G16H 70/60* (2018.01)

(58) Field of Classification Search
CPC ........ G16H 50/20; G16H 10/60; G16H 40/67; G16H 50/30; G16H 50/50; G16H 70/60; A61B 5/445; G06Q 30/0631
See application file for complete search history.

(56) References Cited

U.S. PATENT DOCUMENTS 10,365,156 B2     7/2019  Gonzalez et al.
2010/0185064 A1*  7/2010  Bandic ............... A61B 5/444
                                                                 600/306
(Continued)

FOREIGN PATENT DOCUMENTS

WO    2015/051013 A1   4/2015
WO    2019/036589 A1   2/2019
(Continued)

OTHER PUBLICATIONS

Drakai et al, Air pollution and the skin, 2 Front. Environ. Science (May 15, 2014) (Year: 2014).*
(Continued)

*Primary Examiner* — Jordan L Jackson
(74) *Attorney, Agent, or Firm* — Christensen O'Connor Johnson Kindness PLLC

(57) ABSTRACT

A computer system and the computer-implemented method of generating and providing skincare product recommendations to a subject. The method comprises determining, by a computing device, an exposure amount of a pollutant impacting a subject's skin; determining, by the computing device, a damage assessment of the subject's skin based on the type of pollutant and amount of pollutant exposure; and providing, by the computing device, at least one skincare product recommendation to the subject, wherein the recommendation is directed to repair or prevent damage to the skin provided in the damage assessment.

5 Claims, 4 Drawing Sheets

(51) Int. Cl.
  *G16H 50/50*  (2018.01)
  *G16H 70/60*  (2018.01)

(56) References Cited

U.S. PATENT DOCUMENTS

| | | | |
|---|---|---|---|
| 2012/0321759 A1* | 12/2012 | Marinkovich | A61B 5/442 |
| | | | 356/402 |
| 2015/0041663 A1 | 2/2015 | Oliver et al. | |
| 2015/0102208 A1 | 4/2015 | Appelboom et al. | |
| 2015/0177055 A1 | 6/2015 | Lian et al. | |
| 2017/0023509 A1* | 1/2017 | Kim | G01N 33/0075 |
| 2018/0150896 A1* | 5/2018 | Parkkinen | G06Q 30/0271 |
| 2018/0374567 A1 | 12/2018 | Toumazou et al. | |
| 2019/0080801 A1 | 3/2019 | Klos et al. | |

FOREIGN PATENT DOCUMENTS

| | | | |
|---|---|---|---|
| WO | 2020/142728 A1 | 7/2020 | |
| WO | 2021/003344 A1 | 1/2021 | |

OTHER PUBLICATIONS

Claudia Juliano and Giovanni Antonio Magrini, Cosmetic Functional Ingredients from Botanical Sources for Anti-Pollution Skincare Products, 5(1) Cosmetics 1-18 (Feb. 6, 2018) (Year: 2018).*
Borghi et al., Miniaturized Monitors for Assessment of Exposure to Air Pollutants: A Review, 14(8) Int. J. Environ. Res. Public Health (Year: 2017).*
Methods for sampling and analysis of chemical pollutants in indoor air, World Health Organization (Sep. 23, 2020)[WHO] (Year: 2020).*
Araviiskaia, et al. "The Impact of Airborne Pollution on Skin", JEADV, vol. 33, pp. 1496-1505 (2019).
French Search Report and Written Opinion dated Oct. 6, 2021, issued corresponding French Application No. 2100514, filed Jan. 20, 2021, see p. 1 of 7 pages.
International Search Report and Written Opinion dated Jan. 27, 2022, issued in corresponding PCT Application No. PCT/US2021/055519, filed Oct. 19, 2021, 14 pages.

* cited by examiner

DEVICE FOR MEASURING SKIN EXPOSURE TO POLLUTANTS OR PROXIMITY TO POLLUTANT SOURCES AND RECOMMENDING PERSONALIZED SKINCARE PRODUCTS

SUMMARY

A wearable sensor device and related computer-implemented method ("App") can measure and report skin-affecting air-borne pollutant exposures and/or use known sources of the air-borne pollutants based on GPS proximity to such sources. The method can then recommend skincare products that are specifically tailored to address the effects from specific pollutants. In one embodiment, a database of "Tables" contain information on the possible skin damage attributable to each air-borne pollutants. Using Tables or other databases make it possible to assess the damage to skin caused by such pollutants and recommends more personalized set of skincare products targeted to repair or prevent or delay the damage done to skin.

In one embodiment, App data management includes time logs of the subject's pollutant exposure, a breakdown of their exposure levels (doses) relative to those that would produce harmful effects on skin, and recommendations on how to treat and avoid these effects using skin products.

The pollutant sensors on this device could be based on Metal-Oxide, Electrochemical, and/or Laser or LED scatting technologies. The pollutant concentration levels measured by the devices sensors are transmitted via Bluetooth to a separate, cellular, or WiFi-connected computing device (i.e., mobile phone, smartphone). These pollutant concentration levels are time-logged by the computing device according to the time at which they are wirelessly received. The computing device can then calculate the total exposure across any time period. Effects of different pollutants on skin relative to exposure amount and duration are understood through prior scientific studies.

With the subject's skin profile understood, the app can determine how close the subject's actual skin exposure is to the various harmful thresholds and/or at what rate they'll reach the thresholds (i.e. if they continue to stay in their present location for X minutes).

A wide variety of products, such as ones rich in B vitamins, and ways to use them can be recommended to mitigate the harmful effects of pollution exposure, but only certain ones and application methods are compatible with the subject's skin type and skin sensitivities and skin characteristics. By knowing the subject's skin profile, the app can make more tailored product suggestions.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
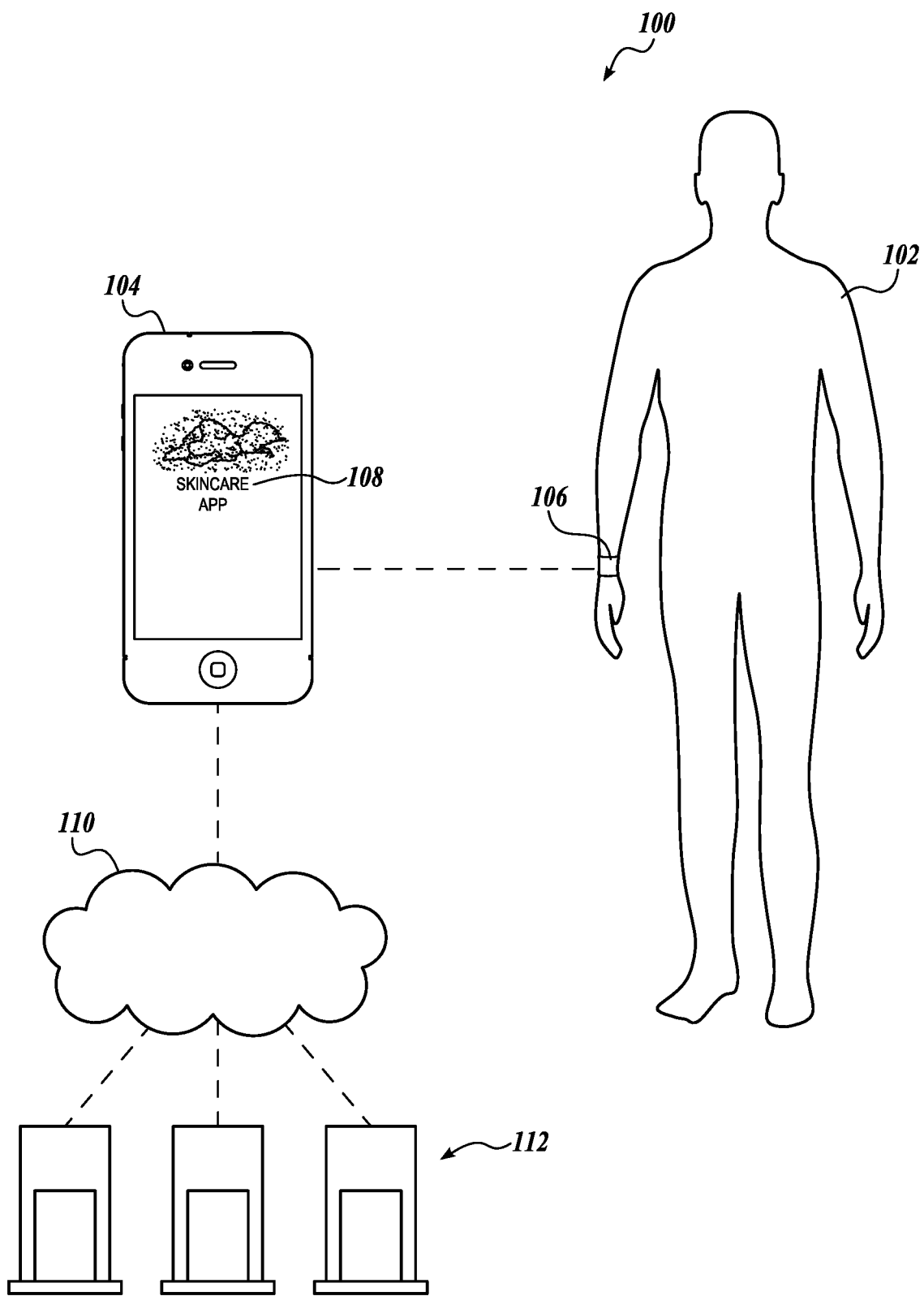
FIG. 1 a schematic diagram that illustrates one embodiment of a system for generating and providing skincare recommendations to a subject.

Personal air quality sensing products output data (air quality indexes and/or safety alerts) tied to known exposure limits and standards. These limits and standards are generally formulated with respect to the respiratory effects that various pollutants can have. In one embodiment, this disclosure can expand or complement existing air quality indexes and/or safety alerts to bring about greater education and awareness about the skin effects, as opposed to just the respiratory effects, that various pollutants can have, and ultimately recommend skincare products that address these effects.

In one embodiment, a wearable personal device is designed to include sensors that measure air pollutants that are known to have harmful effects on human skin, namely NO2, O3, PM1.0, PM2.5, PM10, PAHs (polyaromatic hydrocarbons) and VOCs (volatile organic compounds). Measured data from the device is transmitted to a connected App, which logs the data and performs time-derivative calculations to determine if the subject has been exposed beyond a scientifically-proven skin safety limit. Alternatively, the app can determine the subject's risk level by knowing the subject's GPS location over time relative to web-mapped sources of the aforementioned pollutants (i.e. freeways, high traffic roads, industrial factories, and construction sites). The App alerts the subject about their exposure levels relative to the skin safety limits and recommends skincare products that are tailored to the different effects the various encountered pollutants have.

High levels of air pollutants indoors or outdoors can detrimentally affect one's skin. Accordingly, one embodiment of the present disclosure is directed to a computer-implemented method and the computer system to make it possible for a subject to understand the damage to skin that can be inflicted by the various pollutants, notifying the subject when possible damage to skin has occurred, and recommending one or more products to mitigate and remedy the skin damage.

As used herein, "pollutant" denotes any elements, molecules, particles, environmental factors and the like. In one embodiment, a pollutant can have an adverse effect on a subject's skin.

In one embodiment, the present disclosure is directed to a computer system and computer-implemented method or App to educate and alert subjects about their exposure (real-time/hourly/daily/lifetime, etc.) to the full range of indoor and outdoor pollutants that can damage their skin.

Studies have shown uptake of air-borne pollutants occurs transdermally. Depending on the pollutant type, several biochemical and clinical effects can occur. UV light may also interact with air-borne pollutants and exacerbate the effects. Studies have shown the air-borne pollutants can lead to increase in production of reactive oxygen species, lipid peroxidation, protein oxidation, and apoptosis (cell death). Studies have also shown that air-borne pollutants can lead to skin aging, such as skin wrinkles on the face and hands, as well as pigment spots due to particulate matter (PM), namely PM10 and PM2.5. Particulate matter exists as dust, smoke, soot, liquid droplets, and organic and inorganic particles. Studies have also shown that air-borne pollutants, such as PM10, PM2.5 and NO2, can lead to acne in some populations. Air-borne pollutants can lead to skin dryness and excess sebum production. Air-borne pollutants through skin uptake have also been linked to inflammatory skin diseases, such as eczema. Some air-borne pollutants linked to atopic dermatitis include PM10, NO2, SO2, and O3.

For an in-depth discussion, see "The Impact of Airborne Pollution on Skin," E. Araviiskais et al., J Eur Acad Dermatol Venereol, 2019 August; 33(8).

There are limits to how much exposure to each pollutant or aggregate of pollutants a subject can encounter before the subject begins to experience skin damage. These limits can be a function of skin type, skin characteristics, medical history, predisposition to certain conditions, and the like. In one embodiment, the computer-implemented method can recommend products and a treatment regimen to correct the skin damage done by exposure to air-borne pollutants or to prevent or delay skin damage in the first place. In one embodiment, because pollutants do not affect persons equally, the products and treatment regimen can be tailored and recommended based on a subject's profile, which can include skin type, skin sensitivities and other distinguishing skin characteristics. Such recommendations can consider not only the subject's profile but the duration and frequency of exposure to each type of pollutant, and recommend only certain products and application methods that are compatible with the subject's skin type and skin sensitivities. By knowing the subject's skin profile, the app can make more tailored product suggestions.

Existing studies that show the relationship of skin damage to pollutant exposure can be used to set the limits on the amount of exposure of each pollutant that triggers a notification to the subject that skin damage is possible by continued exposure. Additionally, new studies can be conducted to learn the affects that pollutants have on subjects based on skin type or other factors. The learning experiments can be conducted over a period of time by measuring the pollutant exposure and recording the effects on skin given certain pollutant exposure levels. A computer-implemented method can also adjust the exposure limits for air-borne pollutants according to factors in each subject's profile. The effects on skin for each subject can then be stored in a subject's profile. In one embodiment, exposure is the measure of the concentration of pollutant over time.

The primary sources of particulate matter and the other listed pollutants are industrial and vehicle combustion, woodsmoke, refining, industrial and vehicle abrasion, road dust, quarrying, milling, and large scale transfer of dusty materials. Particulate matter itself can be comprised of a multitude of the other listed pollutants, depending on environmental factors, such as ozone concentrations. In one embodiment, a subject's profile can include a geographic region where the subject resides.

Accordingly, one embodiment of this disclosure is to quantify skin damage according to the amount of exposure to one or more pollutants based on a subject's profile.

In one embodiment, the present disclosure is directed to a computer system and computer-implemented method to provide subjects with more information on their exposure levels to harmful pollutants as they move through different environments in their daily lives. In one embodiment, the subjects are informed about the harmful effects to allow the subject to purchase a wider range (a set) of skin products specifically targeted to correct or protect against the various effects. In one embodiment, the present disclosure is directed to a computer system and computer-implemented method to guide the subject on skincare products that are tailored to their lifestyle, and particularly to correct for any damage to skin that has occurred or that might occur according to the pollutants to which they are most exposed to.

FIG. 1 is a schematic diagram that illustrates one embodiment of a system 100 for tracking a subject's exposure time to one or more pollutants, assessing damage to the subject's skin inflicted by the one or more pollutants, and recommending a personalized set of skincare products depending on the damage caused by the pollutants, and recommending a skincare product and regimen to prevent or alleviate damage caused by the one or more pollutants.

In the system 100, the subject 102 interacts with a mobile computing device 104. In one embodiment, the mobile computing device 104 is capable of performing the computer-implemented method designated by the Skincare App icon 108. The subject may start the computer-implemented method by touching the icon 108 on a touch-sensitive display of the mobile computing device 104. The computer-implemented method is further described in connection with FIG. 4.

In one embodiment, the mobile computing device 104 may be used to receive exposure data of one or more pollutants from a wearable sensor 106 on the subject 102. Additionally or alternatively, the data may come from one or more sources on the Internet, for example, online sources can report the air quality for a particular location, for example, online sites can provide the amount of ozone (O3), particulate matter (PM), sulfur dioxide (SO2), nitrogen dioxide (NO2) and nitrogen oxides (NOx) for particular geographic locations. The mobile computing device 104 can retrieve pollutant concentrations from known sources of the air-borne pollutants based on GPS proximity to such sources.

A wearable environmental sensor 106 is for measuring concentrations of different types of air-borne pollutants (i.e., CO, CO2, NO2, NOx, SO2, O3, PM2.5, PM10, VOC, PAH, heavy metals) as well as environmental factors, such as temperature and humidity. The amount of air-borne pollutants at given locations is also available for downloading from various publicly accessible sources on the Internet. The mobile computing device 104 decides to use the publicly accessible sources based on a GPS on the mobile computing device 104 detecting whether the subject 102 is within a radius of a known source of pollutant concentration data. Once the concentrations are determined, the concentrations are integrated over the period of time that the subject is exposed to that concentration. As the subject 102 moves from location to location, pollutant concentrations can change.

There are a variety of approaches to making the sensor 106 that senses pollutants that are harmful to skin. In one embodiment, sensor 106 is size and/or power and/or cost agnostic and is equipped with a full array of sensors that individually measure each of the aforementioned pollutants. In one embodiment, the sensor 106 is size and/or power and/or cost conscious and is equipped with a small array of sensors that individually measure a small subset of the aforementioned pollutants. In the latter case, determining the concentrations of the non-sensed pollutants could be achieved by extrapolation through data collected by publicly accessible remote sensing devices (that are not size and/or power and/or cost conscious). In one embodiment, the presence of particulate matter can correlate with the presence of the other listed pollutants, and visa-versa, obviating the need to measure or obtain data for some pollutants. In one embodiment, extrapolation can be used to determine pollutant concentrations through a combination of ascertaining a subject's location through GPS data and using local weather station or satellite data including real time and forecasted weather patterns such as wind speed, wind direction, and pollutant concentrations at a known location. For example, a subject 102 can be at a distant location from a publicly accessible source of pollutant data, the mobile computing device 104 can use the data from the publicly accessible source and apply a dispersion model to extrapolate the concentration at the subject's location. A pollutant dispersion model can be based on wind speed, wind direction, atmospheric pressure, weather patterns, meteorological data, and the like to extrapolate the pollutant concentration at the original source to the pollutant concentration at the subject's distant location. In one embodiment, pollutant levels can be determined based on the subject's geographic location, such as city, town, zip code, and the like.

In one embodiment, the sensor 106 is designed to be portable and worn on or near the subject's body for continuously or periodically measuring the subject's environment indoors and outdoors. In one embodiment, the sensor 106 is designed to be portable and worn as a ring. In one embodiment, the construction or chemistry of the individual pollutant sensors may include metal-oxide, hybrid metal-oxide, electrochemical, MEMs, LED scattering, laser scattering, or fuel cell sensors.

In one embodiment, the amount of pollutant in any environment is transmitted from the sensor 106 via a wireless technology to the mobile computing device 104 running the Skincare App. The Skincare App receives these constantly changing values based on the subject's location and integrates them over time to calculate the type and amount that skin has been impacted by pollutants, determines whether or not the subject's skin has been damaged or is at risk of being damaged, and alerts the subject accordingly, and provides recommendations.

In one embodiment, the mobile computing device 104 is connected to a remote server computer system 112 comprised of one or more server computers via a network, such as the Internet 110. The network may include any suitable networking technology, including but not limited to a wireless communication technology (including but not limited to Wi-Fi, WiMAX, Bluetooth, 2G, 3G, 4G, 5G, and LTE), a wired communication technology (including but not limited to Ethernet, USB, and FireWire), or combinations thereof.

Figure 2:
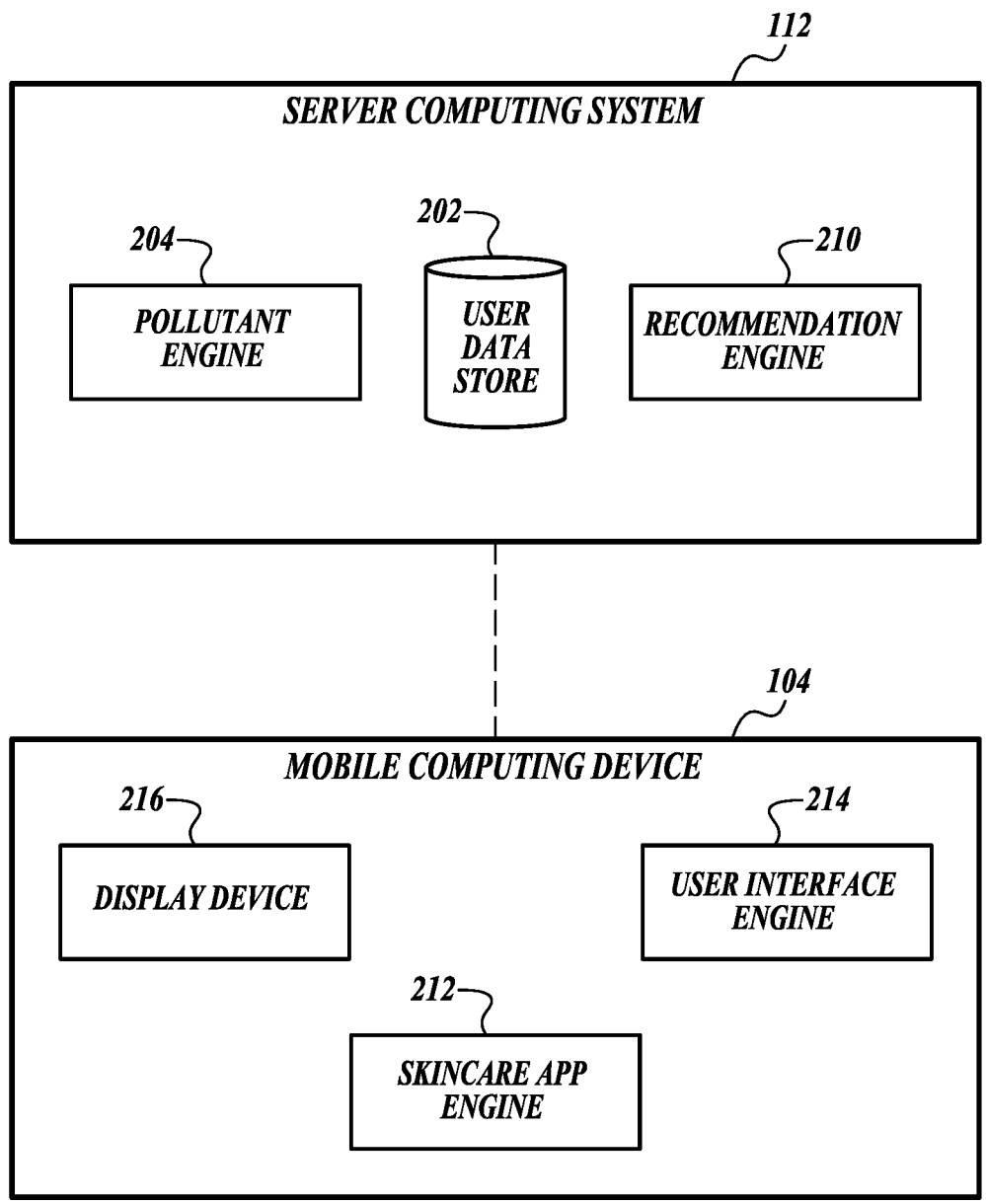
FIG. 2 is a block diagram that illustrates one embodiment of a system that includes a mobile computing device and a server computing device.

FIG. 2 is a block diagram that illustrates a non-limiting example embodiment of a system that includes the mobile computing device 104 and a server computing system 112 according to various aspects of the present disclosure. In one embodiment, the mobile computing device 104 may be a smartphone. In one embodiment, the mobile computing device 104 may be any other type of computing device having the illustrated components, including but not limited to a tablet computing device or a laptop computing device. In one embodiment, the mobile computing device 104 may not be mobile, but may instead be a stationary computing device, such as a desktop computing device. In one embodiment, the illustrated components of the mobile computing device 104 may be within a single housing. In one embodiment, the illustrated components of the mobile computing device 104 may be in separate housings that are communicatively coupled through wired or wireless connections. The mobile computing device 104 also includes other components that are not illustrated, including but not limited to one or more processors, a non-transitory computer-readable medium, a power source, and one or more communication interfaces.

As shown, the mobile computing device 104 includes, at least, a display device 216, a Skincare Application engine 212 (Skincare App engine 212), and a user interface engine 214.

In one embodiment, the display device 216 is an LED display, an OLED display, or another type of display for presenting a user interface. In one embodiment, the display device 216 may be combined with or include a touch-sensitive layer, such that a subject 102 may interact with a user interface presented on the display device 216 by touching the display. In one embodiment, a separate user interface device, including but not limited to a mouse, a keyboard, or a stylus, may be used to interact with a user interface presented on the display device 216.

In one embodiment, the user interface engine 214 is configured to present a user interface on the display device 216 when opening the Skincare App engine 212. The Skincare App engine 212 will cause the user interface engine 214 to display a plurality of user interfaces on the display device 216 relating to a computer-implemented method Skincare App used for the gathering and display of information, including gathering subject specific data, such as skin type, skin sensitivities, current skincare regimen and products used, and the like to create a subject profile. The user interface engine 214 displays user interfaces for recommending a personalized set of skincare products depending on a damage assessment of skin based on the subject's profile, including the subject's skin type and based on the type and amount of pollutants to which the subject's skin has been exposed.

In one embodiment, the user interface engine 214 can present the subject with a questionnaire that is useful to elicit information for determining the subject's profile, such as, but not limited to daily, weekly, and monthly schedules, skin type which can be selected from predetermined menu choices, skincare products currently used, but also provide other options and information.

In one embodiment, the server computing system 112 includes one or more computing devices that each include one or more processors, non-transitory computer-readable media, and network communication interfaces that are collectively configured to provide the illustrated components. In one embodiment, the one or more computing devices that make up the server computing system 112 may be rackmount computing devices, desktop computing devices, or computing devices of a cloud computing service.

As shown, the server computing system 112 includes a user data store 202, a pollutant engine 204, and a recommendation engine 210. In one embodiment, the server computing system 112 is configured to perform data analytics for determining the pollutant concentration as a subject's location changes, integrating the pollutant concentration over time to determine a running total exposure, comparing the pollutant exposure to target exposure levels, determining the pollutants to which the subject has the highest exposure, determining an assessment of the skin damage inflicted by the exposures, and making product recommendations. In one embodiment, the mobile computing device 104 is configured to connect to the server computing system 112 in a cloud computing environment to enable the mobile computing device 104 with the Skincare App engine 212 to use the computing resources of the server computing system 112. In one embodiment, one, some or all of the components of the user data store 202, pollutant engine 204 and a recommendation engine 210 can reside in the mobile computing device 104.

In one embodiment, the user data store 202 is configured to store records for each subject 102 that uses the system. The records may the subject's profile including medical or personal records, such as age, weight, skin type, skin sensitivities, medical risk factors, residence, occupation, athletic activities, schedules, past product recommendations, descriptions of lifestyle, and/or other information collected or determined by the system. For example, a subject's profile can include daily, weekly, and monthly schedules, skin type which can be selected from predetermined menu choices, skincare products currently used.

In one embodiment, the user data store 202 may also contain a database of skincare products, wherein each skincare product is identified by or classified according to one or more attributes. For example, a skincare product can be classified as having one or more of the following attributes: a UV blocker, a moisturizer, a humectant, antioxidant source, hyaluronic acid source, collagen source, and vitamin B. In this manner, the recommendation engine 210 can recommend products that more precisely directed to the type of damage caused by a particular pollutant.

In one embodiment, the user data store 202 may also contain a database of skin types. Skin types may be grouped according to color, composition, melanin types and content, or any combination of two or more factors. In one embodiment, the skincare product recommendations are based on one or more attributes in the subject's profile. In one embodiment, each subject can be assigned to one or more skin types. Each skin type can be related through a series of Tables that relate the skin type to the damage that is inflicted by each pollutant and the exposure amount of pollutant. For example, a Table can quantify the type and amount of damage caused by a certain pollutant according to the amount of exposure to such pollutant for each skin type or another subject attribute. A Table has the exposure limits at which a pollutant is capable of inflicting skin damage. The exposure limits can be adjusted based on one or more attributes in the subject's profile. The Tables also quantify the skin damage, so that a skincare product can be recommended that is specifically targeted to repair or prevent the damage according to a treatment regimen including the skincare product dosage and frequency. Additionally, skin type is one subject attribute according to which skin damage can be categorized. In one embodiment, a combination of subject attributes are stored in Tables to create multi-dimensional relationships for assessing skin damage based on skin type and one or more subject attributes. As can be appreciated, there can be a multiplicity of Tables for each skin type and each additional subject attribute to cover each pollutant and the amount of pollutant to assess the skin damage. In one embodiment, a weighting factor can be applied to subject attributes to increase the weight of the subject attributes which most affect an assessment of skin damage, and consequently the skincare product recommendation.

In one embodiment, the pollutant engine 204 may be configured to process the data acquired by a wearable pollutant sensor 106 to determine pollutant levels and exposure times of the subject's skin to one or more pollutants. In one embodiment, the pollutant engine 204 acquires the pollutant concentrations from publicly accessible sources based on a subject's GPS location or extrapolates the pollutant concentrations from the publicly accessible sources based on dispersion modeling. In one embodiment, measured data from the device is transmitted to a connected App, which logs the data and performs time-derivative calculations to determine if the subject has been exposed beyond scientifically-proven or studied skin safety limits. Alternatively, the App can determine the subject's risk level by knowing the subject's GPS location over time relative to web-mapped sources of the aforementioned pollutants (i.e. freeways, high traffic roads, industrial factories, and construction sites). The App alerts the subject about their exposure levels relative to the skin safety limits and recommends skincare products that are tailored to the different effects the various encountered pollutants have.

In one embodiment, the pollutant engine 204 may be configured to process the data acquired by online publicly accessible sources reporting the amount of air pollutants at the given location of the subject. In one embodiment, the pollutant engine 204 may be configured to both process the data acquired by the pollutant sensor 106 and data acquired through online publicly accessible sources. In one embodiment, the pollutant engine 204 may be configured to calculate the amount of pollutant exposure on a minute, hourly, daily, weekly, monthly, yearly, or lifetime basis. In one embodiment, the pollutant engine 204 calculates the pollutant concentrations by keeping track of a subject's location by global positioning system (GPS) coordinates.

In one embodiment, the pollutant engine 204 is configured to calculate the subject's exposure to one or more pollutants and integrate the exposure amount over time to determine a total exposure level. The total exposure level can then be compared to the relationship Tables that describe the damage to each particular skin type by type and amount of pollutant. This comparison can be done on an hourly, daily, weekly, monthly, or yearly basis to continually update recommendations for skincare products as more exposure time to pollutants leads to greater and greater damage to one's skin.

In one embodiment, the pollutant engine 204 does not use the same target exposure limits for each subject. In one embodiment, the pollutant engine 204 can adjust the target exposure limit based on each subject's profile, and in particular, the subject's skin type and skin characteristics. Additionally, other attributes in a subject's profile may be used to increase or decrease target exposure limit for a pollutant to deem when skin damage has occurred. These attributes may describe medical risk factors that indicate certain subject are more predisposed to a skin condition. Additionally, the exposure limits may be adjusted according to UV exposure, since UV has been linked to interacting with some air-borne pollutants. In one embodiment, the exposure limits of pollutants are adjusted based on the interaction between the pollutants and UV or other light. For example, while a pollutant can lead to a skin damaging effect, the effect can be multiplied through photoactivation by light of a certain wavelength. Also, because light of a certain wavelength and pollutants can independently lead to similar skin damage effects, if the pollutant exposure limit is related to the onset of these effects, then prior light exposure, such as UV, can reduce the pollutant exposure limit, and visa-versa. In other words, UV or other light can have the same skin damaging effect as a pollutant, and the pollutant exposure limit should be determined based on the combined exposure of the pollutant and the UV or other light. Therefore, in one embodiment, the exposure limits of pollutants are adjusted down based the amount of light exposure, such as UV, of the subject or the pollutant exposure limit is based on counting both the amount of exposure of the pollutant as well as the amount of exposure to UV or other light that has the same skin damaging effect as the pollutant. The compounding effect is not limited to UV or light, but, can also include other pollutants that have the same skin damaging effect. In other words, exposure limits are based on counting the exposure amounts of more than one pollutant. In this case, there is a total exposure limit for a group of pollutants that have the same skin damaging effect. In one embodiment, the exposure limit of a pollutant or a group of pollutants is a sum total based on counting the exposure amounts of the pollutants that have the same damaging skin effects. In one embodiment, the amount of exposure of pollutants that contribute to the same skin damaging effect can be weighted according to the proportional contribution each pollutant has to cause the skin damaging effect. The pollutant engine 204 uses the subject's profile or other attributes to set the target exposure limit.

In one embodiment, the recommendation engine 210 is configured to generate recommendations of skincare products for protection against one or more pollutants or for care of damaged skin caused by pollutants. In one embodiment, the recommendation engine 210 provides a set of skincare product recommendations based on an assessment of the damage done to skin. In one embodiment, the skin damage assessment is based on the pollutants to which the subject has the highest exposure. In one embodiment, the skin damage assessment is based on determining when pollutant exposure levels are a certain percentage from reaching or have reached a target limit set for that pollutant and based on the subject's profile.

In one embodiment, the recommendation engine 210 can further calculate recommendations based on the subject's profile, such as currently used products. In this manner, the recommendation engine 210 is able to provide a personalized set of skincare products unique to the subject.

In one embodiment, products for recommendations are stored in a manner that associates the products' qualities to the skin damage the product aims to repair or prevent. In this way, once skin damage is calculated, an appropriate product can be recommended.

In one embodiment, skincare products may include water-based or oil-based creams, foams, soaps, sprays, and the like. Skincare products may also include other ingredients, such as UV blockers, moisturizers, humectants, antioxidants, hyaluronic acid, collagen, EDTA, vitamin B, carriers such as oil and water, and the like. In one embodiment, a skincare product is categorized according to the damage it is aimed to help. The products can be associated with the Tables that show relationships between skin type or any subject attribute, the pollutants, and skin damage inflicted by pollutants.

"Engine" refers to logic embodied in hardware or software instructions, which can be written in a programming language, such as C, C++, COBOL, JAVA™, PHP, Perl, HTML, CSS, JavaScript, VBScript, ASPX, Microsoft .NET™, Go, and/or the like. An engine may be compiled into executable programs or written in interpreted programming languages. Software engines may be callable from other engines or from themselves. Generally, the engines described herein refer to logical modules that can be merged with other engines, or can be divided into sub-engines. The engines can be stored in any type of computer-readable medium or computer storage device and be stored on and executed by one or more general purpose computers, thus creating a special purpose computer configured to provide the engine or the functionality thereof.

"Data store" refers to any suitable device configured to store data for access by any one or more computing device. One example of a data store is a highly reliable, high-speed relational database management system (DBMS) executing on one or more computing devices and accessible over a high-speed network. Another example of a data store is a key-value store. However, any other suitable storage technique and/or device capable of quickly and reliably providing the stored data in response to queries may be used, and the computing device may be accessible locally instead of over a network, or may be provided as a cloud-based service. A data store may also include data stored in an organized manner on a computer-readable storage medium, such as a hard disk drive, a flash memory, RAM, ROM, or any other type of computer-readable storage medium. One of ordinary skill in the art will recognize that separate data stores described herein may be combined into a single data store, and/or a single data store described herein may be separated into multiple data stores. In one embodiment, the data store 202 is used for storing the relationship Tables that link subjects' profiles, subjects' attributes, subjects' skin type, pollutant type, pollutant exposure level, pollutant exposure limits that inflict skin damage, the type of skin damage, and skincare products with the dosage and frequency, which are then used in making assessments of skin damage and providing skincare product and treatment regimen recommendations directed to the specific skin damage. In one embodiment, an advantage is provided when the skin damage assessment takes into consideration subject attributes from a subject profile.

Figure 3:
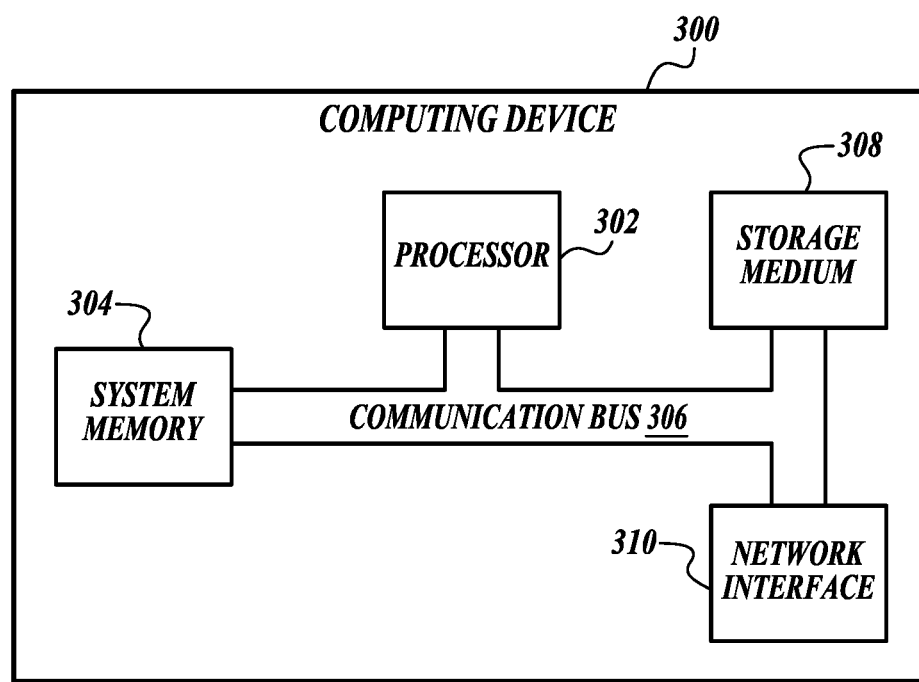
FIG. 3 is a block diagram that illustrates one embodiment of a computing device appropriate for use as a computing device with embodiments of the present disclosure.

FIG. 3 is a block diagram that illustrates aspects of an exemplary computing device 300 appropriate for use as a mobile computing device of the present disclosure. While multiple different types of computing devices were discussed above, the exemplary computing device 300 describes various elements that are common to many different types of computing devices. While FIG. 3 is described with reference to a mobile computing device, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 300 may be any one of any number of currently available or yet to be developed devices.

In its most basic configuration, the computing device 300 includes at least one processor 302 and a system memory 304 connected by a communication bus 306. Depending on the exact configuration and type of device, the system memory 304 may be volatile or nonvolatile memory, such as read only memory ("ROM"), random access memory ("RAM"), EEPROM, flash memory, or similar memory technology. Those of ordinary skill in the art and others will recognize that system memory 304 typically stores data and/or program modules that are immediately accessible to and/or currently being operated on by the processor 302. In this regard, the processor 302 may serve as a computational center of the computing device 300 by supporting the execution of instructions.

As further illustrated in FIG. 3, the computing device 300 may include a network interface 310 comprising one or more components for communicating with other devices over a network. Embodiments of the present disclosure may access basic services that utilize the network interface 310 to perform communications using common network protocols. The network interface 310 may also include a wireless network interface configured to communicate via one or more wireless communication protocols, such as WiFi, 2G, 3G, LTE, WiMAX, Bluetooth, Bluetooth low energy, and/or the like. As will be appreciated by one of ordinary skill in the art, the network interface 310 illustrated in FIG. 3 may represent one or more wireless interfaces or physical communication interfaces described and illustrated above with respect to particular components of the computing device 300.

In the exemplary embodiment depicted in FIG. 3, the computing device 300 also includes a storage medium 308. However, services may be accessed using a computing device that does not include means for persisting data to a local storage medium. Therefore, the storage medium 308 depicted in FIG. 3 is optional. In any event, the storage medium 308 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data. In this regard, the system memory 304 and storage medium 308 depicted in FIG. 3 are merely examples of computer-readable media.

Suitable implementations of computing devices that include a processor 302, system memory 304, communication bus 306, storage medium 308, and network interface 310 are known and commercially available. For ease of illustration and because it is not important for an understanding of the claimed subject matter, FIG. 3 does not show some of the typical components of many computing devices. In this regard, the computing device 300 may include input devices, such as a keyboard, keypad, mouse, microphone, touch input device, touch screen, tablet, and/or the like. Such input devices may be coupled to the computing device 300 by wired or wireless connections including RF, infrared, serial, parallel, Bluetooth, Bluetooth low energy, USB, or other suitable connections protocols using wireless or physical connections. Similarly, the computing device 300 may also include output devices such as a display, speakers, printer, etc. Since these devices are well known in the art, they are not illustrated or described further herein.

Figure 4:
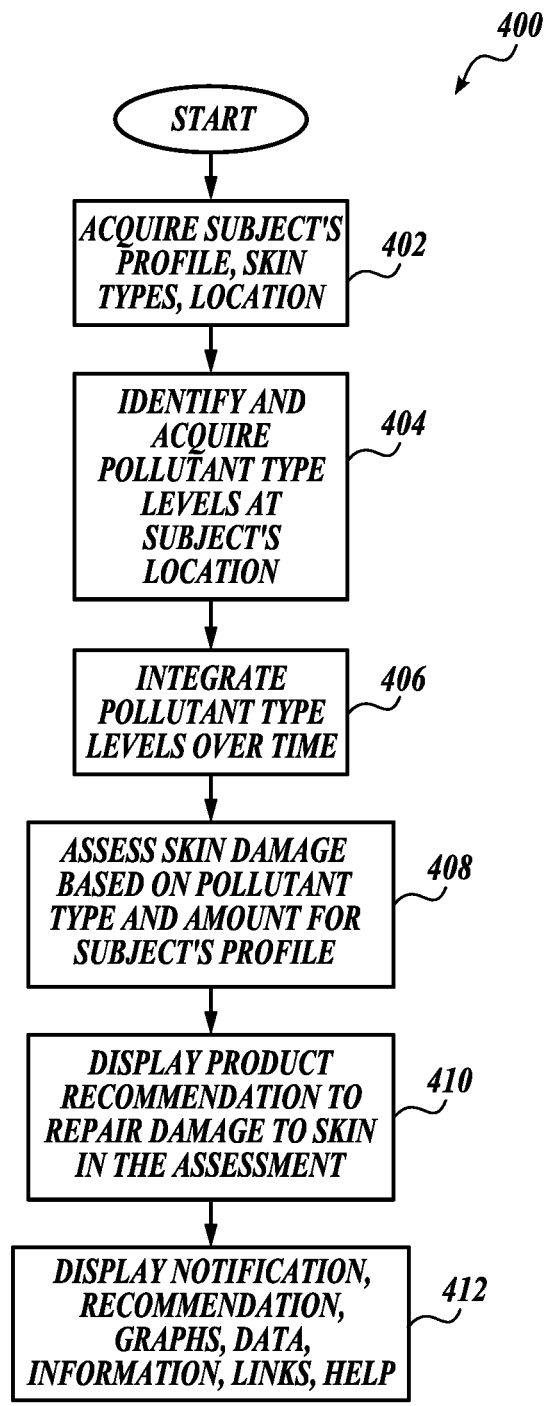
FIG. 4 is a flowchart that illustrates one embodiment of a method of generating and providing recommendations to a subject.

FIG. 4 is a flowchart that illustrates a non-limiting example embodiment of a computer-implemented method of recording the type and amount of pollutant to which a subject with a particular attribute, such as skin type has been exposed, assessing the damage or possible damage that can be inflicted by the particular type and amount of pollutant, and then, recommending a skincare product directly targeted to repair or prevent the specific skin damage. In one embodiment, a damage assessment of skin takes into consideration the subject's profile, including, for example, skin type or other attributes in the subject profile. The effects on skin from the various air-born pollutants are described in published works or can be the subject for new studies. The method 400 may be implemented, in one example, by the mobile computing device 104 alone or in combination with one or more server computing devices 112. The computer-implemented method is performed by the Skincare App engine 212, pollutant engine 204, recommendation engine 210, user interface engine 214 communicating with each other and with the user data store 202.

In one embodiment, the method may be performed in part by the mobile computing device 104 and in part by the remote server computer system 112. In one embodiment, the mobile computing device 104 is configured to upload data regarding the subject to an external system or server (such as a cloud-based system). Such data may include the subject profile. In one embodiment, a subject profile includes the subject's skin type, skin characteristics, such as color, composition, melanin types and content, medical risk factors, and the like. Skin sensitivities may also be included in the subject profile, so that the method does not result in recommending products that would lead to a skin rash or allergy.

The computer-implemented method 400 may start by clicking on the Skincare App icon 108 on the display of the mobile computing device 104 to open the Skincare App engine 212.

From the start block, the Skincare App engine 212 proceeds to block 402, where the Skincare App engine 212 receives the subject's 102 profile, location, and skin type, for example.

If a profile has not been provided, the Skincare App engine 212 can use the user interface engine 214 to present to the subject, a questionnaire with questions regarding all the relevant information needed to complete the profile. The subject can enter the information through the display device 216 through the use of menus with preselected lists of choices. In one embodiment, the Skincare App engine 212 accesses the user data store 202 for the profile and other information.

In one embodiment, the subject's location can be constantly determined through a GPS in the mobile computing device 104. In this way, the subject's location can be continuously monitored and updated in real time. In one embodiment, the location is used to retrieve information about the pollutant levels at that subject's current location or dispersion modeling can be used to calculate the pollutant levels at the subject's GPS location from a known pollutant level at a distant location. The subject's current location can be continuously updated as the subject moves from location to location.

In block 404, the pollutant engine 204 identifies the type of pollutants the subject's skin is currently being exposed to, the pollutant concentration, and begins to record the exposure time for each pollutant as the subject moves from location to location to keep track of a total running amount of pollutant exposure. More specifically, the pollutant engine 204 identifies the types and amount of pollutants impacting skin on a subject. If the subject is wearing clothes or otherwise shielding his or her skin form exposure, the pollutant engine 204 has a way to adjust the pollutant exposure amount by taking into consideration the amount of protection from pollutants clothes provides.

In one embodiment, the pollutant concentrations can be retrieved from publicly accessible online sources on air quality by receiving air pollutant information from known sources within a radius of the subject's GPS location or the amount of pollutants can be determined by one or more sensors 106 worn by the subject 102 or placed on the mobile computing device 104. These pollutant concentration levels are time-logged by the computing device according to the time at which they are wirelessly received. The computing device can then calculate the total exposure across any time period.

Depending on the sensor 106, data can be processed by the sensor 106 or the mobile computing device 104. In one embodiment, the subject 102 scans the sensor 106 with the mobile computing device 104 to establish a connection between the sensor 106 and the mobile computing device 104. Communication pairing is performed between the sensor 106 and the mobile computing device 104 when the two devices are within an acceptable wireless communication range of each other. In one embodiment, the sensor 106 includes RFID and antenna for the subject to obtain the data wirelessly. The pollutant concentration levels measured by the sensor 106 are transmitted via Bluetooth to a separate, cellular, or WiFi-connected device (i.e., mobile phone, smartphone).

To illustrate how a pollutant sensor may operate, the sensor 106 works by inducing and electronic current proportional to a certain pollutant concentration. The amount of such pollutant can then be converted and stored as voltage, which is a measurement of cumulative pollutant exposure over time. Pollutant exposure can be reported on a per unit of time basis, such as daily, weekly, monthly, etc. The voltage is read each time as the subject scans the sensor 106. From block 404, the method proceeds to block 406.

In block 406, whether the pollutant engine 204 receives the pollutant levels from sensor 106 or online sources, the pollutant engine 204 keeps track of the pollutant levels at the subject's location and the time at the location to integrate the pollutant level of each pollutant into a running exposure amount over time. In this manner, the pollutant engine 204 can keep track of the subject's location and the pollutant levels at each location throughout the subject's daily routine. This can be done automatically by the mobile computing device 104, or the subject can decide when to turn the Skincare App engine 212 on and off. The subject 102 can also follow their pollutant level exposure over time. The pollutant engine 204 can keep a running total of pollutant exposure in any increments of time, such as by the minute, hour, day, week, month, or year. From block 406, the method proceeds to block 408.

In block 408, the pollutant engine 204 assesses the damage inflicted on the subject's skin by considering the type and total exposure amount for each pollutant. Effects of different pollutants on skin relative to exposure amount and duration are understood through prior scientific studies or through performing new studies. With the subject's skin profile understood, the pollutant engine 204 can determine how close the subject's actual skin exposure is to the various harmful thresholds and/or at what rate they'll reach the thresholds (i.e. if they continue to stay in their present location for X minutes). The damage assessment may be performed through the use of data Tables that store relationships of the damage caused by each pollutant for each subject attribute, such as skin type. Skin types may be grouped according to color, composition, melanin content, or any combination of two or more factors. The Tables may also store incremental damage caused by higher exposure of pollutants. The Tables contain the pollutant exposure targets that determine the limits at which skin damage is likely to occur or has occurred for each pollutant.

In one embodiment, the pollutant exposure limit is the amount of a given pollutant that when considered alone leads to skin damage. However, skin damage effects can be the result of more than one pollutant. The pollutant engine 204 can take other factors to derive pollutant exposure limits. In one embodiment, the exposure limits of pollutants are adjusted based on the interaction between the pollutants and light, such as UV. Also, because light and pollutants can independently lead to similar skin damage effects, if the pollutant exposure limit is related to the onset of these effects, then prior light exposure, such as UV, can reduce the pollutant exposure limit, and visa-versa. Therefore, in one embodiment, the exposure limits of pollutants are adjusted down based the amount of light exposure of the subject or the pollutant exposure limit is based on counting both the exposure of the pollutant as well as the exposure to UV or other light that has the same skin damaging effect as the pollutant. In one embodiment, the pollutant exposure limit is a sum total of the exposure amounts of pollutants or light that have the same skin damaging effect.

The limits can be adjusted for each subject based on the attributes in the subject's profile. For example, a Table can have incremental limits for each pollutant to quantify greater damage according to greater exposures to pollutants, and consequently recommend higher doses or increase the frequency of treatments with skincare products. Tables may also store any damage that is the caused by two or more pollutants or interactions of pollutants. In performing a skin damage assessment, the pollutant engine 204 uses the subject's profile to assign skin damage, including skin type or other attributes personal to the subject, the type and amount of each pollutant, and then, uses the Tables to find the type of skin damage inflicted by the pollutants. From block 408, the method enters block 410.

In block 410, the recommendation engine 210 can display a notification to the subject detailing the pollutant exposure and the damage being caused to the skin. In one embodiment, the user interface engine 214 may display the recommended skincare products based on the skin damage assessment. The skin damage assessment may contain the type of damage, the amount of damage, a location on the skin, and the like. The skin damage assessment can be viewed by the subject on the mobile computing device. The Tables storing the skin damage related by type and amount of pollutant exposure can also store the product or products that aim to help repair and prevent the skin damage. In one embodiment, the user interface engine 214 can display the type of skin damage, its causes, helpful information, and the like. In one embodiment, the user interface engine 214 creates tutorials on how to use the skincare products. The user interface engine 214 may create and download protocols for a regimen or routine on how to use the skincare products. The user interface engine 214 can coach, track usage and compare the tracked usage to the protocol, the regimen, and the routine. Therefore, the Skincare App 212 can keep track of each subject's profile and pollutant exposure levels and can provide recommendations on product selection, styling methods, skincare regimens that are based on the levels of pollutants that can damage skin, an assessment of damage caused to particular skin types by the type and exposure amounts according to individual pollutants. Additionally, the user interface engine 214 can be used to make a purchase of any products related to the recommended skincare products. From block 410, the method proceeds to block 412.

In block 412, the user interface engine 214 can display helpful graphs, data, information, warnings, useful links, and help relating to the skin damage and the pollutants. In one embodiment, the user interface engine 214 may create a display on the mobile computing device 104 with an indication of the subject risk of skin damage in percentage form, along with a category label such as "low", "moderate," or "high." A graph may also be displayed that tracks the pollutant exposure levels over time. The subject may recall any prior history on exposure levels for the pollutants.

In one embodiment, the computer-implemented method 400 is continuously running to update the types of pollutants and the integrated amount of exposure to pollutants over time to update its skin damage assessment and make new or updated recommendations.

While illustrative embodiments have been illustrated and described, it will be appreciated that various changes can be made therein without departing from the spirit and scope of the invention.

The embodiments of the invention in which an exclusive property or privilege is claimed are defined as follows:

1. A system comprising:
    a sensor that detects one or more air-borne pollutants, including:
        chemistry employed for sensing one or more pollutant is selected from one of a metal-oxide, hybrid metal-oxide, electrochemical, MEMs, LED scattering, laser scattering, or fuel cell sensor; and
        records an amount of the one or more air-borne pollutant as a voltage, wherein the one or more pollutant is one of at least CO, CO2, NO2, NOx, SO2, O3, polyaromatic hydrocarbons, volatile organic compounds, and heavy metal; and
    a smartphone includes:
        wireless communication;
        a global positioning system; and
        a computer-readable medium having stored thereon instructions that execute steps to:
            obtaining a subject's GPS coordinates via the global positioning system;
            detect when a subject is within a radius of an internet accessible source of pollutant concentration data based on the GPS coordinates;
            download the concentration data of air-borne pollutants from the internet accessible source;
            integrate the concentration data over time while the subject is within the radius;
            keep track of the subject's location and the pollutant concentration data as the subject moves locations;
            communicate wirelessly with the sensor to determine an exposure amount of the one or more pollutant impacting a subject's skin when the sensor is scanned using the smartphone;
            communicate wirelessly with the sensor to determine an exposure amount of UV light impacting a subject's skin when the sensor is scanned using the smartphone;
            calculate a target exposure limit at which a harmful skin effect occurs using the sensor voltage and the internet accessible source of pollutant concentration data for the one or more pollutant, including adjusting the target exposure limit using a combined exposure of the one or more pollutant and the UV light, wherein the harmful skin effect is related to one or more of skin aging, wrinkles, pigment spots, acne, dryness, excess sebum, inflammatory skin disease, atopic dermatitis;
            determine whether the amount of exposure exceeds the target exposure limit.

2. The system of claim 1, wherein the computer-readable medium further has stored thereon instructions that executes a step to:
    continuously integrate a total amount of exposure for each pollutant impacting the subject's skin.

3. The system of claim 1, wherein the computer-readable medium further has stored thereon instructions that executes a step to:
    determine the target exposure limit based on a sum total of exposure amounts of more than one pollutants.

4. The system of claim 1, wherein the computer-readable medium further has stored thereon instructions that executes steps to:
    time-log pollutant concentration levels according to a time at which they are wirelessly received, and
    to calculate total exposure across a time period.

5. The system of claim 1, wherein the computer-readable medium further has stored thereon instructions that execute a step to:
    send a notification of the closeness of the amount of exposure to the target exposure limit; and
    send a notification of the time when the target exposure limit will be reached at a present location.

* * * * *